United States Patent

Burdge et al.

[11] Patent Number: 6,025,301
[45] Date of Patent: Feb. 15, 2000

[54] INDANONE HERBICIDE COMPOSITIONS AND USE THEREOF

[75] Inventors: Ernest Leroy Burdge, Pennsburg; Manuel Victor Nunez, Souderton; Lori Ann Spangler, Churchville, all of Pa.

[73] Assignee: Rohm and Haas Company, Philadelphia, Pa.

[21] Appl. No.: 09/033,031

[22] Filed: Mar. 2, 1998

Related U.S. Application Data

[60] Provisional application No. 60/039,293, Mar. 4, 1997.

[51] Int. Cl.[7] .................................................. A01N 43/56
[52] U.S. Cl. ............................................. 504/281; 504/282
[58] Field of Search ...................................... 504/281, 282

[56] References Cited

FOREIGN PATENT DOCUMENTS 2 223 946  10/1988  United Kingdom .

*Primary Examiner*—S. Mark Clardy
*Attorney, Agent, or Firm*—Clark R. Carpenter

[57] ABSTRACT

This invention relates to an indanone herbicidal composition comprising a compound having the general formula

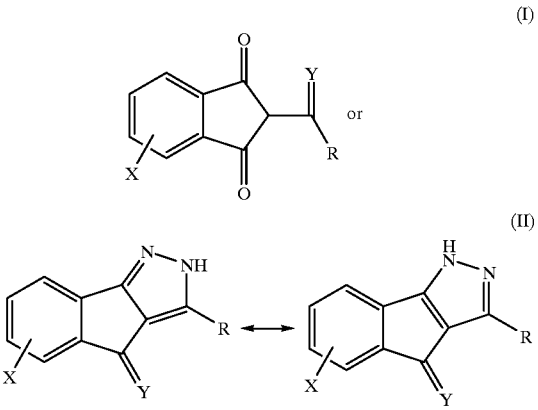

wherein
  Y is an oxygen atom or a hydrazono group,
  R is alkyl or substituted alkyl,
  X is a hydrogen atom or is one to three substituents independently selected from the group consisting of halo, alkyl, cycloalkyl, alkenyl, cycloalkenyl, alkynyl, haloalkyl, haloalkenyl, haloalkynyl, alkoxy, alkylthio, alkylsulfonyl, alkylsulfinyl, phenyl, phenalkyl, phenalkenyl, phenalkynyl, cyano, haloalkoxy, 1,3-dioxalan-2-yl, hydroxyimino and nitro, and
  an agronomically acceptable carrier.

The invention also discloses a method of use of these compositions.

7 Claims, No Drawings

INDANONE HERBICIDE COMPOSITIONS AND USE THEREOF

This is a nonprovisional application of prior pending provisional application Ser. No. 60/039,293 filed Mar. 4, 1997.

The need continues for novel and improved herbicidal compositions. This is particularly so since the targets of herbicides can become resistant to known herbicides over time and after use of such compositions. Additionally, economic and environmental considerations can favor herbicides having different modes of performance than those currently used. This invention relates to compositions comprising indanone herbicides and an agronomically acceptable carrier and the use thereof as broad spectrum herbicides which are effective against both monocot and dicot weed species in postemergence applications. This invention also teaches methods of preparing these compounds as well as methods of using the compounds as herbicides.

Some of the compounds which comprise the herbicidal compositions of this invention are disclosed in *Industrial and Engineering Chemistry*, 34, 494–497 (1942) as being useful as insecticides. However, the use of these compounds as herbicides is not disclosed or suggested. Other compounds which comprise the herbicidal —compositions of this invention are disclosed in *J. Pharm. Sci.*, 67, 1377 (1978). However, only the synthesis of these compounds is described and no agricultural utility is suggested.

UK Patent Application GB 2 223 946 A discloses a herbicidal composition, comprising as active ingredient at least one indeno-[1,2-c]pyrazol-4-one derivative of the formula

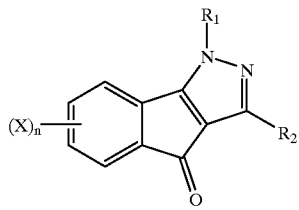

wherein $R_1$ is an acyl group, $R_2$ is an optionally substituted alkyl or cycloalkyl group and X represents halogen, nitro, alkyl, haloalkyl, alkoxy or haloalkoxy, and n is 0, 1 or 2, which is useful for preventing or combating undesired plant growth at a locus. However, none of the compounds comprising the herbicidal compositions of this invention are disclosed or suggested.

One embodiment of this invention relates to an indanone herbicidal composition comprising a compound having the formula

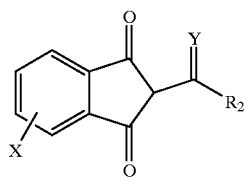

wherein

Y is an oxygen atom (O) or a hydrazono group ($H_2N$—N),

R is a straight chain or branched chain ($C_1$–$C_8$)alkyl or a straight chain or branched chain ($C_1$–$C_8$)alkyl substituted with cyano, ($C_1$–$C_4$)alkoxy or one or more halo, X is a hydrogen atom (H) or is one to three substituents independently selected from the group consisting of bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$)alkenyl, halo($C_2$–$C_6$)alkynyl, ($C_1$–$C_{12}$)alkoxy, ($C_1$–$C_{12}$)alkylthio, ($C_1$–$C_{12}$)alkylsulfonyl, ($C_1$–$C_{12}$)alkylsulfinyl, phenyl, phen($C_1$–$C_{12}$)alkyl, phen($C_2$–$C_{12}$)alkenyl, phen($C_2$–$C_{12}$)alkynyl, cyano, halo($C_1$–$C_{12}$)alkoxy, 1,3-dioxalan-2-yl, hydroxyimino and nitro, and an agronomically acceptable carrier.

In a preferred embodiment of this invention,

R is a straight chain or branched chain ($C_1$–$C_6$)alkyl or a straight chain or branched chain ($C_1$–$C_6$)alkyl substituted with cyano, ($C_1$–$C_4$)alkoxy or one or more halo, and X is a hydrogen atom or is one to three substituents independently selected from the group consisting of bromo, chloro, fluoro, ($C_1$–$C_4$)alkyl, cyclo($C_3$–$C_6$)alkyl, ($C_2$–$C_6$)alkenyl, cyclo($C_3$–$C_6$)alkenyl, ($C_2$–$C_6$)alkynyl, halo($C_1$–$C_6$)alkyl, halo($C_2$–$C_6$)alkenyl, halo($C_2$–$C_4$)alkynyl, ($C_1$–$C_6$)alkoxy, ($C_1$–$C_6$)alkylthio, ($C_1$–$C_6$)alkylsulfonyl, ($C_1$–$C_6$)alkylsulfinyl, phenyl, phen($C_1$–$C_6$)alkyl, phen($C_2$–$C_6$)alkenyl, phen($C_2$–$C_6$)alkynyl, cyano, halo($C_1$–$C_6$)alkoxy, 1,3-dioxalan-2-yl, hydroxyimino and nitro.

In a more preferred embodiment of this invention,

Y is an oxygen atom,

R is a straight chain or branched chain ($C_1$–$C_4$)alkyl or a straight chain or branched chain ($C_1$–$C_4$)alkyl substituted with cyano, ($C_1$–$C_2$)alkoxy or one or more halo, and X is a hydrogen atom or is one to two substituents independently selected from the group consisting of bromo, chloro, fluoro, ($C_1$–$C_2$)alkyl, ($C_2$–$C_3$)alkenyl, ($C_2$–$C_3$)alkynyl, halo($C_1$–$C_2$)alkyl, halo($C_2$–$C_3$)alkenyl, halo($C_2$–$C_3$)alkynyl, ($C_1$–$C_2$)alkoxy, ($C_1$–$C_2$)alkylthio, phenyl, phen($C_1$–$C_2$)alkyl, cyano, halo($C_1$–$C_2$)alkoxy and nitro.

In an even more preferred embodiment,

R is is a straight chain or branched chain ($C_3$–$C_4$)alkyl or a straight chain or branched chain ($C_3$–$C_4$)alkyl substituted with cyano, ($C_1$–$C_2$)alkoxy or one or more halo, and X is a hydrogen atom or is one to two substituents independently selected from the group consisting of bromo, chloro, fluoro, ($C_1$–$C_2$)alkyl, halo($C_1$–$C_2$)alkyl, ($C_1$–$C_2$)alkoxy, cyano, halo($C_1$–$C_2$)alkoxy and nitro.

In a most preferred embodiment,

R is n-propyl, isopropyl, isobutyl or tert-butyl, and

X is a hydrogen atom or chloro.

Another embodiment of this invention relates to an indanone herbicidal composition comprising a compound having the formula

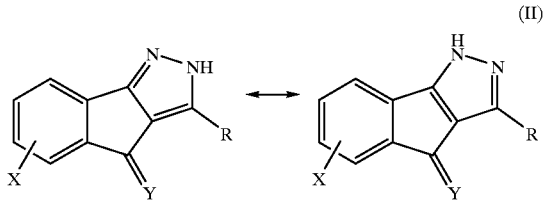

(II)

wherein

Y is an oxygen atom (O) or a hydrazono group (H₂N—N),

R is a straight chain or branched chain ($C_1$–$C_8$)alkyl or a straight chain or branched chain ($C_1$–$C_8$)alkyl substituted with cyano, ($C_1$–$C_4$)alkoxy or one or more halo, X is a hydrogen atom (H) or is one to three substituents independently selected from the group consisting of bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$)alkenyl, halo($C_2$–$C_6$)alkynyl, ($C_1$–$C_{12}$)alkoxy, ($C_1$–$C_{12}$)alkylthio, ($C_1$–$C_{12}$)alkylsulfonyl, ($C_1$–$C_{12}$)alkylsulfinyl, phenyl, phen($C_1$–$C_{12}$)alkyl, phen($C_2$–$C_{12}$)alkenyl, phen($C_2$–$C_{12}$)alkynyl, cyano, halo ($C_1$–$C_{12}$)alkoxy, 1,3-dioxalan-2-yl, hydroxyimino and nitro, and an agronomically acceptable carrier.

The two structures shown for compounds of formula (II) represent both tautomeric forms of the compounds. The compound itself cannot be isolated in either form since the actual compound exists in a state of equilibrium between the two isomeric forms.

In a preferred embodiment of this invention,

R is a straight chain or branched chain ($C_1$–$C_6$)alkyl or a straight chain or branched chain ($C_1$–$C_6$)alkyl substituted with cyano, ($C_1$–$C_4$)alkoxy or one or more halo, and X is a hydrogen atom or is one to three substituents independently selected from the group consisting of bromo, chloro, fluoro, ($C_1$–$C_4$)alkyl, cyclo($C_3$–$C_6$)alkyl, ($C_2$–$C_6$)alkenyl, cyclo($C_3$–$C_6$)alkenyl, ($C_2$–$C_6$)alkynyl, halo($C_1$–$C_6$)alkyl, halo($C_2$–$C_6$)alkenyl, halo($C_2$–$C_4$)alkynyl, ($C_1$–$C_6$)alkoxy, ($C_1$–$C_6$)alkylthio, ($C_1$–$C_6$)alkylsulfonyl, ($C_1$–$C_6$)alkylsulfinyl, phenyl, phen($C_1$–$C_6$)alkyl, phen($C_2$–$C_6$)alkenyl, phen($C_2$–$C_6$)alkynyl, cyano, halo($C_1$–$C_6$)alkoxy, 1,3-dioxalan-2-yl, hydroxyimino and nitro.

In a more preferred embodiment of this invention,

Y is an oxygen atom,

R is a straight chain or branched chain ($C_1$–$C_4$)alkyl or a straight chain or branched chain ($C_1$–$C_4$)alkyl substituted with cyano, ($C_1$–$C_2$)alkoxy or one or more halo, and X is a hydrogen atom or is one to two substituents independently selected from the group consisting of bromo, chloro, fluoro, ($C_1$–$C_2$)alkyl, ($C_2$–$C_3$)alkenyl, ($C_2$–$C_3$)alkynyl, halo($C_1$–$C_2$)alkyl, halo($C_2$–$C_3$)alkenyl, halo($C_2$–$C_3$)alkynyl, ($C_1$–$C_2$)alkoxy, ($C_1$–$C_2$)alkylthio, phenyl, phen($C_1$–$C_2$)alkyl, cyano, halo($C_1$–$C_2$)alkoxy and nitro.

In an even more preferred embodiment,

R is is a straight chain or branched chain ($C_3$–$C_4$)alkyl or a straight chain or branched chain ($C_3$–$C_4$)alkyl substituted with cyano, ($C_1$–$C_2$)alkoxy or one or more halo, and X is a hydrogen atom or is one to two substituents independently selected from the group consisting of bromo, chloro, fluoro, ($C_1$–$C_2$)alkyl, halo($C_1$–$C_2$)alkyl, ($C_1$–$C_2$)alkoxy, cyano, halo($C_1$–$C_2$)alkoxy and nitro.

In a most preferred embodiment,

R is n-propyl, isopropyl, isobutyl or tert-butyl, and

X is a hydrogen atom or chloro.

Yet another embodiment of this invention relates to a method of controlling a weed comprising applying a herbicidally effective amount of a composition comprising an indanone compound having the general formula (I) or (II) and an agronomically acceptable carrier to the weed, to the locus of the weed or to the growth medium of said weed.

The following examples, tables and experimental procedures are provided for guidance to the practitioner and are not meant to limit the scope of the invention which is defined by the claims.

TABLE IA

Structures and Melting Points of Formula (I) Tested Compounds

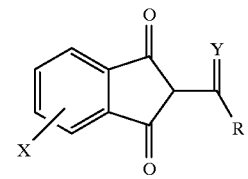

| Compound | X | Y | R | m.p. ° C. |
|---|---|---|---|---|
| 1 | H | O | C(CH₃)₃ | 104–107 |
| 2 | Cl | O | CH(CH₃)₂ | 102–105 |
| 3 | H | O | CH(CH₃)₂ | 91–93 |
| 4 | H | NNH₂ | C(CH₃)₃ | 137–143 |
| 5 | H | O | CH₂CH₂CH₃ | oil |
| 6 | H | O | CH₂CH(CH₃)₂ | 64–66 |
| 7 | Cl | O | C(CH₃)₃ | 99–101 |

TABLE IB

Structures and Melting Points of Formula (II) Tested Compounds

| Compound | X | Y | R | m.p. ° C. |
|---|---|---|---|---|
| 8 | H | O | CH(CH₃)₂ | 145–148 |
| 9 | H | O | C(CH₃)₃ | 185–190 |
| 10 | H | NNH₂ | CH(CH₃)₂ | 221–225 |

The names of the compounds listed in Tables IA and IB are:

| Compound | Name |
|---|---|
| 1 | 1H-indene-1,3(2H)-dione, 2-(2,2-dimethyl-1-oxopropyl) |
| 2 | 1H-indene-1,3(2H)-dione, 2-(2-methyl-1-oxopropyl)-5-chloro |
| 3 | 1H-indene-1,3(2H)-dione, 2-(2-methyl-1-oxopropyl) |
| 4 | 1H-indene-1,3(2H)-dione, 2-[1-(hydrazono)-2,2-dimethylpropyl] |
| 5 | 1H-indene-1,3(2H)-dione, 2-(1-oxobutyl) |
| 6 | 1H-indene-1,3(2H)-dione, 2-(3-methyl-1-oxobutyl) |
| 7 | 1H-indene-1,3(2H)-dione, 2-(2,2-dimethyl-1-oxopropyl)-5-chloro |
| 8 | indeno[1,2-c]pyrazol-4(1H)-one, 3-(1-methylethyl) |
| 9 | indeno[1,2-c]pyrazol-4(1H)-one, 3-(1,1-dimethylethyl) |
| 10 | indeno[1,2-c]pyrazol-4(1H)-hydrazono, 3-(1-methylethyl) |

EXPERIMENTAL PROCEDURES

EXAMPLE 1

Preparation of 1H-indene-1,3(2H)-dione, 2-(2,2-dimethyl-1-oxopropyl)-5-chloro (Compound 7)

A suspension of sodium methoxide (6.2 g, 114 mmol) in toluene (400 mL) was prepared and treated with dimethyl 4-chlorophthalate (19 g, 83 mmol) and pinacolone (10 g, 100 mmol) and the mixture heated to reflux for 18 h. After cooling, the mixture was partitioned between water (320 mL) and ether (100 mL). The ether layer was discarded. The aqueous phase was made acidic with concentrated hydrochloric acid, then extracted with ether (2×250 mL). The ether was dried and concentrated under reduced pressure to yield a solid which was boiled with methanol (40 mL) to which water was added (10 mL). The solid which formed was collected and dried to yield the title compound (3.9 g).

Other analogs were prepared in a similar fashion from various dimethyl phthalates and ketones:

1H-indene-1,3(2H)-dione, 2-(2-methyl-1-oxopropyl)-5-chloro (Compound 2) from dimethyl 4-chlorophthalate and 3-methylbutan-2-one.

1H-indene-1,3(2H)-dione, 2-(2-methyl-1-oxopropyl) (Compound 3) from dimethyl phthalate and 3-methylbutan-2-one.

1H-indene-1,3(2H)-dione, 2-(1-oxobutyl) (Compound 5) from dimethyl phthalate and 2-pentanone.

EXAMPLE 2

Preparation of 1H-indene-1,3(2H)-dione, 2-[1-(hydrazono)-2,2-dimethylpropyl] (Compound 4)

A solution of 1H-indene-1,3(2H)-dione, 2-(2,2-dimethyl-1-oxopropyl) (2.0 g, 9.2 mmol) in methanol (10 mL) and para-dioxane (10 mL) was cooled to 0 C. To this was added sodium acetate (0.8 g, 10 mmol) and hydrazine hydrochloride (0.7 g, 10 mmol) and water (10 mL). After 30 minutes, the cooling bath was removed and the mixture allowed to stir for 18 h. The reaction mixture was concentrated under reduced pressure and partitioned between ethyl acetate (100 mL) and water (40 mL). The organic phase was dried and concentrated under reduced pressure to yield the title compound as a solid (1.2 g).

EXAMPLE 3

Preparation of indeno[1,2-c]pyrazol-4(1H)-one, 3-(1,1-dimethylethyl) (Compound 9)

A solution of 1H-indene-1,3(2H)-dione, 2-(2,2-dimethyl-1-oxopropyl) (2.3 g, 10 mmol) in ethanol (20 mL) was treated with hydrazine (0.5 g, excess) and acetic acid (1 mL). The mixture was heated to reflux for 18 h. The reaction mixture was cooled to room temperature and concentrated under reduced pressure. The resulting product was placed on a 1.5×7 inch silica gel column and eluted with 20–60% ethyl acetate/hexane. Fractions containing the desired product were combined (1.3 g).

Compounds 1, 6, 8 and 10 are commercially available materials.

The indanone compositions of this invention are useful as postemergence herbicides. Postemergence herbicides are applied after the plants have emerged and during their growth period. The embodied materials generally show selectivity to several agronomically important crops such as corn, sorghum, sugarcane, macadamia nuts, conifers and guava.

The indanone compositions of the present invention can be applied to various loci such the soil or the foliage. For such purposes these compositions can be used as solutions or as formulations. The compounds comprising the compositions are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The indanone compositions can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 0.011 kg. to about 11.2 kg. per hectare of the active ingredient.

The indanone compositions of the invention can also be mixed with fertilizers or fertilizing materials before their application. In one type of solid fertilizing composition in which the indanone compounds can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The indanone compound will commonly be from about 5% to about 25% of the fertilizing composition. These compositions provide fertilizing materials which promote the rapid growth of desired plants, and at the same time control the growth of undesired plants.

For some applications, one or more other herbicides may be added to the compositions of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;

2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester;
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2-yl)aminocarbonyl]benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
N-(4-isopropylphenyl)-N,N'-dimethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5-triazin-2-yl)aminocarbonyl)-2-(2-chloroethoxy)-benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[(4-methoxy-6-methyl-1,3,5-triazin-2-yl)aminocarbonyl]aminosulfonyl]-2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxy]-2-nitrobenzoate;
5-[2-chloro-4-(trifluoromethyl)phenoxyl]-N-(methylsulphony)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-α,α-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;

2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-α,α-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol [1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired. Preferred mixing partners with the indanone herbicidal compositions of the present invention include, but are not limited to, bentazon Na salt, metolachlor, simazine, cyanazine, alachlor, propachlor, bromoxynil octanoate ester, dicamba K salt, acetochlor, butylate, 2,4-D, ametryne, asulam and amitrole.

The herbicidal activity of the indanone compounds comprising the compositions of the present invention towards a number of common weeds was evaluated using a greenhouse method of testing. Using the greenhouse test methods described below, the indanone compounds 1–10 of the present invention were evaluated for control of weeds selected from the following:

| Common Name | Code | Scientific name |
| --- | --- | --- |
| Monocots | | |
| Barnyardgrass | (BYG) | *Echinochloa crus-galli* |
| Crabgrass | (CRB) | *Digitaria sanguinalis* |
| Green Foxtail | (FOX) | *Setana viridis* |
| Perennial Ryegrass | (RYE) | *Lolium perenne* |
| Dicots | | |
| Hairy Beggarticks | (BID) | *Bidens pilosa* |
| Nightshade | (NS) | *Solanum nigrum* |
| Smartweed | (SMT) | *Polygonum lapathifolium* |
| Velvetleaf | (VEL) | *Abutilon theophrasti* |

The following greenhouse test procedure was employed. Seeds of selected plants were planted in flats or pots. For these postemergence tests, the seeds were allowed to germinate and grow for 10 to 21 days. Before application, each series of test plants was selected for uniformity of size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 25 or 50 gallons per acre at the rate of application in grams per hectare (g/ Ha) specified in the below tables. About two or three weeks after application of the test compound, the stage of growth of the plant was observed. Each species was evaluated on a scale of 0–100 in which 0 equals no activity and 100 equals total control.

The results of the greenhouse tests are shown in Table II. Dose rates are listed in g/Ha. The indicator (-) means that the compound was not tested for that particular weed species.

TABLE II

| GREENHOUSE POSTEMERGENCE APPLICATION DATA | | | | | | | | |
| --- | --- | --- | --- | --- | --- | --- | --- | --- |
| Compound | DOSE | BID | NS | SMT | VEL | BYG | CRB | FOX | RYE |
| 1 | 2400 | 0 | 25 | 60 | 0 | 10 | 0 | 25 | 5 |
| 2 | 2400 | 100 | 70 | 25 | 10 | 10 | 15 | 15 | 10 |
| 3 | 2400 | 0 | 0 | 0 | 0 | 15 | 0 | 20 | 10 |
| 4 | 2400 | 60 | 100 | 0 | 65 | 80 | 65 | 35 | 10 |
| 5 | 4800 | (-) | (-) | (-) | 55 | 25 | (-) | 70 | (-) |
| 6 | 2400 | 50 | 0 | 30 | 0 | 0 | 0 | 0 | 15 |
| 7 | 2400 | 45 | 0 | 100 | 30 | 25 | 30 | 85 | 0 |
| 8 | 2400 | 100 | 80 | 0 | 95 | 98 | 80 | 100 | 30 |
| 9 | 2400 | 100 | 100 | 100 | 100 | 100 | 100 | 100 | 45 |
| 10 | 2400 | 100 | 50 | 35 | 30 | 65 | 75 | 100 | 20 |

We claim:

1. An indanone herbicidal composition comprising a compound having the formula

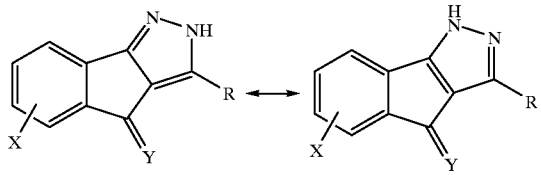

wherein

Y is an oxygen atom or a hydrazono group,

R is a straight chain or branched chain $(C_1-C_8)$alkyl or a straight chain or branched chain $(C_1-C_8)$alkyl substituted with cyano, $(C_1-C_4)$alkoxy or one or more halo, X is a hydrogen atom or is one to three substituents independently selected from the group consisting of bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino and nitro, and an agronomically acceptable carrier.

2. The composition of claim 1 wherein

R is a straight chain or branched chain $(C_1-C_6)$alkyl or a straight chain or branched chain $(C_1-C_6)$alkyl substituted with cyano, $(C_1-C_4)$alkoxy or one or more halo, and X is a hydrogen atom or is one to three substituents independently selected from the group consisting of bromo, chloro, fluoro, $(C_1-C_4)$alkyl, cyclo$(C_3-C_6)$alkyl, $(C_2-C_6)$alkenyl, cyclo$(C_3-C_6)$alkenyl, $(C_2-C_6)$alkynyl, halo$(C_1-C_6)$alkyl, halo$(C_2-C_6)$alkenyl, halo$(C_2-C_4)$alkynyl, $(C_1-C_6)$alkoxy, $(C_1-C_6)$alkylthio, $(C_1-C_6)$alkylsulfonyl, $(C_1-C_6)$alkylsulfinyl, phenyl, phen$(C_1-C_6)$alkyl, phen$(C_2-C_6)$alkenyl, phen$(C_2-C_6)$alkynyl, cyano, halo$(C_1-C_6)$alkoxy, 1,3-dioxalan-2-yl, hydroxyimino and nitro.

3. The composition of claim 2 wherein

Y is an oxygen atom,

R is a straight chain or branched chain $(C_1-C_4)$alkyl or a straight chain or branched chain $(C_1-C_4)$alkyl substituted with cyano, $(C_1-C_2)$alkoxy or one or more halo, and X is a hydrogen atom or is one to two substituents independently selected from the group consisting of bromo, chloro, fluoro, $(C_1-C_2)$alkyl, $(C_2-C_3)$alkenyl, $(C_2-C_3)$alkynyl, halo$(C_1-C_2)$alkyl, halo$(C_2-C_3)$alkenyl, halo$(C_2-C_3)$alkynyl, $(C_1-C_2)$alkoxy, $(C_1-C_2)$alkylthio, phenyl, phen$(C_1-C_2)$alkyl, cyano, halo$(C_1-C_2)$alkoxy and nitro.

4. The composition of claim 3 wherein

R is is a straight chain or branched chain $(C_3-C_4)$alkyl or a straight chain or branched chain $(C_3-C_4)$alkyl substituted with cyano, $(C_1-C_2)$alkoxy or one or more halo, and X is a hydrogen atom or is one to two substituents independently selected from the group consisting of bromo, chloro, fluoro, $(C_1-C_2)$alkyl, halo$(C_1-C_2)$alkyl, $(C_1-C_2)$alkoxy, cyano, halo$(C_1-C_2)$alkoxy and nitro.

5. The composition of claim 4 wherein

R is n-propyl, isopropyl, isobutyl or tert-butyl, and

X is a hydrogen atom or chloro.

6. A method of controlling a weed comprising applying a herbicidally effective amount of a composition of claim 1 to the weed, to the locus of the weed or to the growth medium of said weed.

7. The method of claim 6 wherein the locus of the weed is a corn, sorghum, sugarcane, macadamia nuts, conifers or guava crop.

* * * * *